(12) United States Patent
Chu et al.

(10) Patent No.: US 6,235,040 B1
(45) Date of Patent: May 22, 2001

(54) SINGLE PULL WIRE MULTIPLE BAND LIGATOR

(75) Inventors: Michael S. H. Chu, Brookline; Yem Chin, Burlington, both of MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/157,577

(22) Filed: Sep. 21, 1998

(51) Int. Cl.[7] .................................................. A61B 17/10
(52) U.S. Cl. ............................................................ 606/139
(58) Field of Search .................................. 606/139, 140, 606/141, 144, 148

(56) References Cited

U.S. PATENT DOCUMENTS 5,968,056 * 10/1999 Chu et al. ............................. 606/140

* cited by examiner

Primary Examiner—Henry J. Recla
Assistant Examiner—Vy Q. Bui
(74) Attorney, Agent, or Firm—Kenyon & Kenyon

(57) ABSTRACT

A ligating band dispenser comprises a substantially cylindrical first support surface capable of holding a plurality of first ligating bands. The first support surface has a first channel extending substantially axially therethrough and a plurality of first slots extending away from a distal end thereof through at least a portion of the first support surface. A plurality of increased diameter abutting portions define a plurality of segments of a pull line extending through the slots with each of the abutting portions being retained within the channel by contact with a corresponding one of the slots. Each of the segments loops around a corresponding one of the ligating bands to releasably couple the pull line to the ligating bands.

32 Claims, 14 Drawing Sheets

US 6,235,040 B1

SINGLE PULL WIRE MULTIPLE BAND LIGATOR

FIELD OF THE INVENTION

The present invention relates generally to the field of tissue ligation, and more particularly to an improved device for dispensing ligating bands.

BACKGROUND INFORMATION

Physicians have used elastic ligating bands to treat lesions, including internal hemorrhoids and mucositis and for performing mechanical hemostasis. The object of such ligation is to position a ligating band, which is usually elastic, over the targeted lesion or blood vessel section by first stretching the band beyond its undeformed diameter and then drawing the tissue to be ligated within the band. Thereafter the band is released so that it contracts, applying inward pressure on the section of tissue caught within the band. The effect of the inward pressure applied by the band is to stop all circulation through the targeted tissue, thereby causing the tissue to die. The body then sloughs off the dead tissue and the tissue passes naturally through the body.

U.S. Pat. No. 5,398,844 to Zaslavsky et al. ("the Zaslavsky patent") and U.S. Pat. No. 5,356,416 to Chu et al. ("the Chu patent"), which are incorporated herein by reference, describe ligating band dispensing devices each including a substantially cylindrical support surface over which elastic ligating bands are stretched. The cylindrical support surface is typically attached to the distal end of an endoscope which is advanced into the body to a target area. A user then applies suction through the endoscope to draw the tissue to be ligated into the cylindrical support surface and releases a ligating band to contract around the tissue.

Previous ligating band dispensers allowed a user to dispense only a single ligating band at a time. That is, after a single ligating band was dispensed, if a user wanted to ligate another portion of tissue, the user would remove the device from the patient's body, load a new ligating band on the device and reinsert the device to the desired area within the patient's body. The devices of the Zaslavsky and Chu patents allow a user to place several ligating bands at desired locations without removing the device from the patient's body to reload ligating bands. However, the Zaslavsky patent teaches the use of multiple strings to deploy the multiple bands (i.e. a separate pull string for each band), while the Chu patent teaches a ligator including multiple housing and piston segments to deploy the multiple bands.

U.S. Pat. No. 5,624,453 to Ahmed shows a device in which multiple cords 103 extend from a line element 105 to engage each of a plurality of ligating bands 50. Specifically, each of the cords 103 includes a plurality of knots 109 which are located proximally of each band 50 so that, when the line 105 is drawn proximally, each of the cords 103 is drawn proximally with one knot 109 on each cord 103 being moved distally an equal distance. Each of the knots 109 is substantially equally spaced about the circumference of the adapter 102 so that the force applied via the line 105 is distributed around the circumference of each of the bands 50 and an incrementally increasing amount of slack ensures that when the distal most remaining band 50 is deployed, none of the remaining bands is moved toward the edge of the adapter 102.

However, the multiple cords 103 extend distally across the field of vision of the endoscope impairing the vision of the operator. In addition, these symmetrically distributed cords 103 cause the line 105 to extend substantially centrally through the lumen of the endoscope, thereby limiting the operator's ability to use this lumen to operate other devices. Finally, as seen in FIG. 18, the cords 103 extend within the adapter 102 in a substantially cone shaped form, coming together at the connector 106. This may impede the drawing of lesion tissue into the adapter 102 under suction or, alternatively, may result in unintended deployment of the bands 50 as the tissue drawn into the adapter 102 pushes the connector 106 proximally. Finally, assembling a device as described in this patent can be very labor intensive—requiring proper placement of all of the multiple cords 103 and the corresponding slack segments with each of the cords being arranged so that the knots 109 are properly positioned with respect to the bands 50.

SUMMARY OF THE INVENTION

The present invention is directed to a ligating band dispenser, comprising a substantially cylindrical support surface capable of holding a plurality of ligating bands, the support surface having a channel extending substantially axially therethrough, wherein a plurality of slots extend away from a distal end of the support surface through at least a portion of the support surface. The ligating band dispenser includes a pull line having a plurality of increased diameter abutting portions, each of the abutting portions having a diameter greater than a diameter of the pull line, the abutting portions defining a plurality of segments therebetween, wherein the pull line extends through the slots with each of the abutting portions being retained within the channel by contact with a corresponding one of the slots and wherein each of the segment segments loops around a corresponding one of the ligating bands.

DETAILED DESCRIPTION OF THE INVENTION

Figure 1:
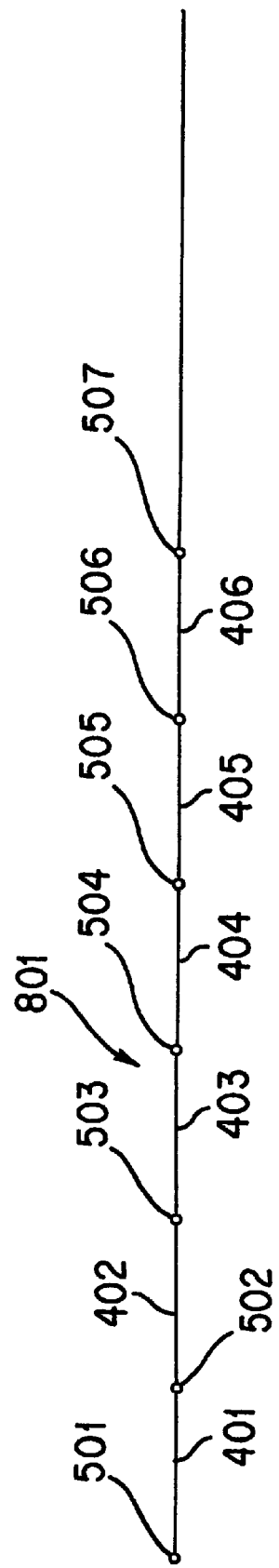
FIG. 1 is a schematic drawing illustrating an exemplary pull string according to the present invention.

FIG. 1 shows a schematic view of a pull string 801 according to the present invention. Pull string 801 includes, for example, a plurality of knots 501–507 arranged along its length, the knots being separated by a plurality of string segments 401–406. It can be understood that many different elements could take the place of and perform the function of knots 501–507. For example, solid objects could be glued, clamped, or otherwise fixed to the pull string 801. Alternatively (or in addition), a liquid could be applied to points on the string, the liquid beading and then hardening into a solid. Other variations are possible. For purposes of clarity, the description below employs only the term "knot," but that term is intended to include those embodiments described above as well as other suitable embodiments. It should thus not be construed as a limitation on the present invention.

Figure 2:
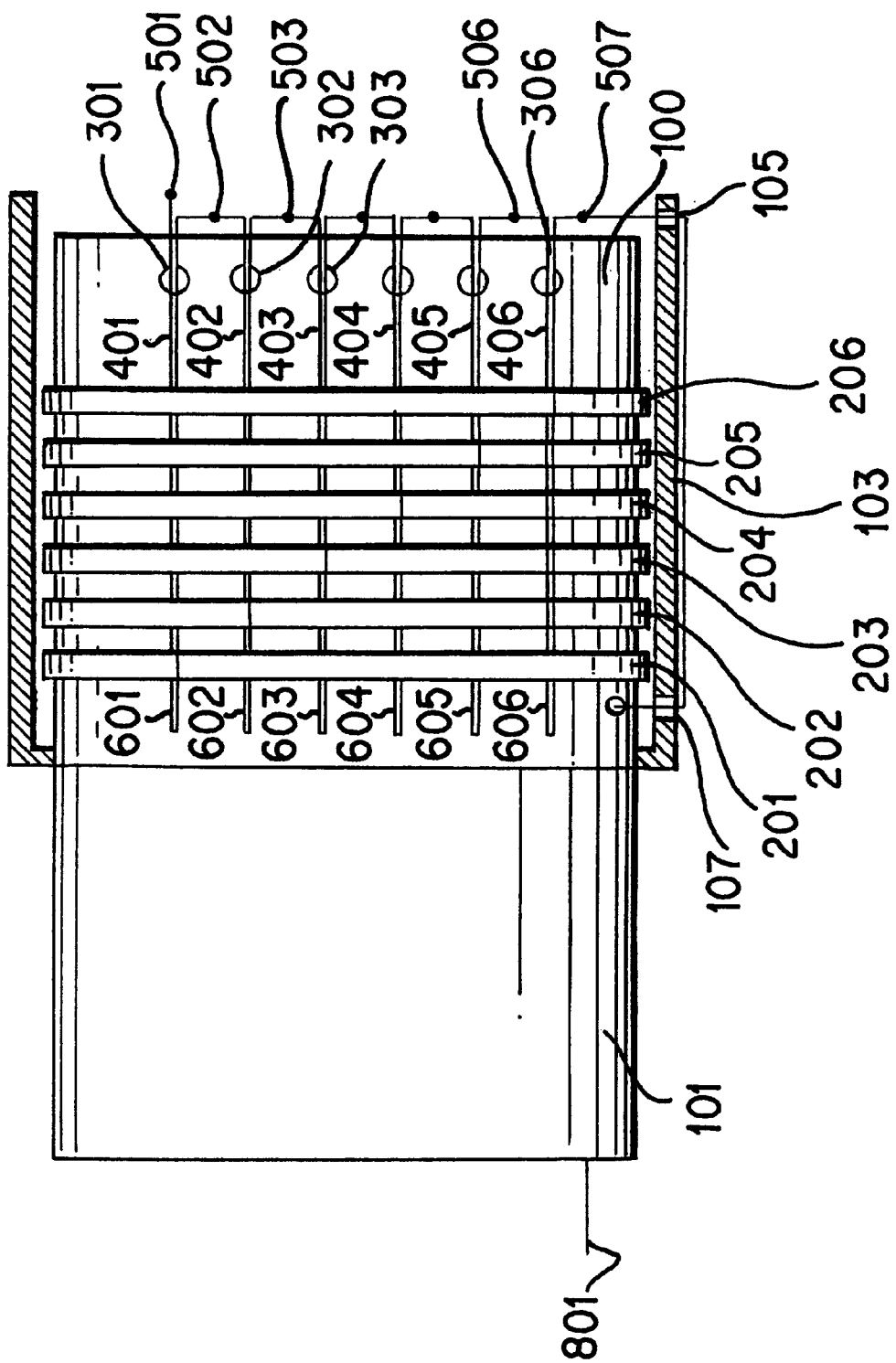
FIG. 2 is a side view of an exemplary ligating band dispenser according to the present invention.

FIG. 2 shows an embodiment of a ligating band dispenser including the pull string of FIG. 1. The ligating band dispenser includes, for example, a substantially cylindrical housing having a distal support surface 100 and an adaptor 101 designed to couple the ligating band dispenser to an endoscope or other suitable device (not shown). While being substantially cylindrical, the housing may have features not shown in the drawings such as a slight taper towards the distal end (the distal end being located to the right in the Figures). The ligating band dispenser includes, for example, a substantially cylindrical channel 111 (not shown on the side views) extending therethrough. Support surface 100 includes, for example, a plurality of slots 301–306, which are smaller, for example, than the knots 501–506. FIG. 2 illustrates a ligating band dispenser holding, for example, six ligating bands 201–206, but the ligating device may include any suitable number of bands.

The ligating band dispenser may also include, for example, a substantially cylindrical casing 103 attached to the ligating band dispenser, for example, at or near the proximal end of the distal support surface 100. Casing 103 may cover the distal support surface 100 to ease insertion of the device and to ensure that bands 201–206 remain in place while the device travels through the body. As can be seen from FIG. 2, casing 103 may extend further distally than support surface 100. Casing 103 may also include, for example, an outlet hole 105 near its distal end so that pull string 801 may be drawn beyond support surface 100, outside casing 103 and away from the lesion and bands 201–206. Further, casing 103 may include an inlet hole 107 near its proximal end so that pull string 801 may be threaded, for example, into adaptor 101 and through the endoscope to the operator.

The arrangement of bands 201–206 and pull string 801 begins, for example, with the proximal-most band 201 (that is, the band appearing furthest to the left of FIG. 2). Knot 501 is placed and retained, for example, behind slot 301. The term "behind" in this context designates a position within channel 111. As shown schematically in the Figures, slots 301–306 may be shaped, for example, to accommodate knots 501–507 in a position behind slots 301–306 and to retain knots 501–507 in place. With knot 501 retained in place, the pull string 801 may be threaded through slot 301, so that pull string 801 is outside the ligating band dispenser, and extended proximally along the distal support surface 100. Band 201 is then stretched over support surface 100 and placed, for example, over pull string 801 near the proximal end of support surface 100. Once band 201 is in place, the pull string 801 may, for example, be looped back over band 201. Pull string 801 is then threaded, for example, down through slot 301 and back up through slot 302. In this manner, knot 502 is retained, for example, between slots 301 and 302 (e.g. behind slot 302). Therefore, as shown in the exemplary arrangement of FIG. 2, string segment 401 is wrapped around band 201, with any slack portion 601 of string segment 401 resting, for example, along the distal support surface 100 proximal to band 201. Slack portion 601 may, of course, be longer or shorter than pictured in FIG. 2 and other Figures.

With knot 502 retained, for example, behind slot 302, pull string 801 can again be extended proximally along the support surface 100. Band 202 may then be stretched over the support surface 100 and placed, for example, just distal of band 201. For purposes of clarity, FIG. 2 illustrates some distance between the bands 201–206. Bands 201–206, however, may contact each other if desired. Once band 202 is in place, pull string 801 may be looped over band 202 and threaded through slots 302 and 303 so that knot 503 is retained behind slot 303. The slack portion 602 of string segment 402 (the portion of pull string 801 looped around band 202) may extend proximally over the support surface 100 and be tucked under band 201.

In the same manner, pull string 801 may again be extended proximally over support surface 100. Band 203 may then be placed over pull string 801 and support surface 100, and pull string 801 may be looped back over band 203 and wound through the appropriate slots. This process may continue until remaining bands 604–606 are arranged in the same manner. Specifically, each band 604–606 is placed, for example, distally of the previous bands, with the corresponding knot 504–506 retained behind a corresponding slot 304–306. Knot 507 may also be retained, for example, behind slot 306, thereby ensuring that pull string 801 does not migrate distally. It may be noted that, when referring to pull string 801, "distally" refers to a direction along pull string 801 itself away from the operator, without reference to "distal" or "proximal" portions of the support surface 100.

As shown in FIG. 2, the slack portions 603–606 of string segments 403–406 may be extended proximally over the support housing and, for example, over any proximal bands except band 201. Slack portions 603–606 may then, for example, be tucked under band 201. It will understood that as each slack portion 601–606 is placed on support surface 100, the corresponding slack increases in each case unless string segments 401–406 decrease in length. While string segments 401–406 of decreasing length may be employed, in an exemplary embodiment string segments 401–406 are equal or substantially equal in length. In this exemplary embodiment, pull string 801 may then be drawn by a spooler (not shown), which may take up the same amount of thread with rotation, for example the amount of thread required to deploy one of bands 201–206.

To deploy bands 201–206, the ligating band dispenser is fixed, for example, to the end of an endoscope (not shown), inserted into the body, and maneuvered to the desired location. Once the ligating device reaches the desired location, suction, for example, is applied to the lesion as known in the art so that the lesion is drawn, for example, into channel 111. The operator may then draw pull string 801 proximally (or cause pull string 801 to be so drawn), so that string segment 406 arranged around band 206 is drawn, for example, through the outlet hole 105 and proximally to the operator. Pull string 801 thus takes up the slack portion 606 and begins to urge band 206 toward the distal end of support surface 100. Because knot 506 is retained behind slot 306, the portion of the pull string 801 arranged around bands 201–205 is not drawn toward the operator, and bands 201–205 remain in place.

Upon reaching the distal end of the support surface 100, band 206 will deploy to ligate the tissue drawn into the channel 111. The deployment may be facilitated, for example, by a taper or bevel of the distal end of support surface 100 (not shown). With the band deployed, knot 506 is freed from slot 306. When the pull string 801 is further drawn to the operator, knot 506 will exit, for example, the outlet hole 105, allowing band 205 to be deployed in a manner described above. This process may continue with an operator ligating successive portions of tissue with each of the bands 202–206 until all of the bands 202–206 have been deployed.

When the ligating band dispenser is fixed to the distal end of an endoscope, the support surface 100 is preferably oriented so that the point where the string 801 extends from the distal rim of the support surface 100 is as close as possible to the lumen of the endoscope through which the string 801 extends back to the operator. This ensures that the string 801 does not interfere with either the field of vision or the drawing of tissue into the channel 111.

Figure 3:
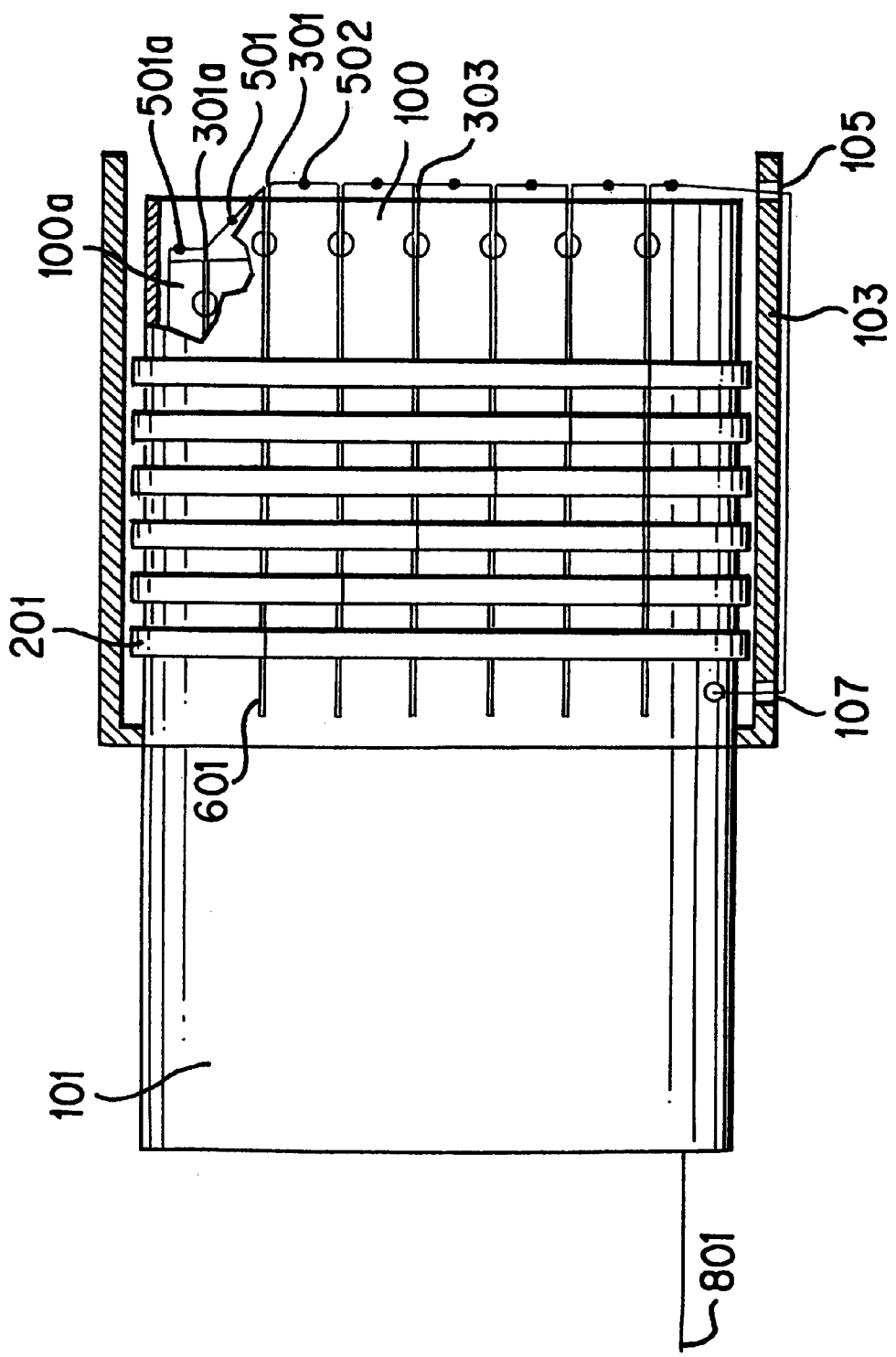
FIG. 3 is a partially cut away side view of an exemplary ligating band dispenser according to the present invention having a second dispensing layer.

FIG. 3 illustrates a second exemplary embodiment of a ligating band dispenser according to the present invention. This second exemplary embodiment includes a second substantially cylindrical support layer 100a disposed, for example, within support layer 100. Second support layer 100a could also be disposed outside support layer 100, for example between support layer 100 and outer casing 103. FIG. 3 also shows support layer 100 extending, for example, further distally than second support layer 100a, but this configuration may also be reversed. Second support layer 100a contains, for example, additional slots (represented by slot 301a), which have the same configuration, for example, as slots 301–306. Second support layer 100a allows the ligating device to hold a greater number of bands without unsuitably extending the length of the ligating band dispenser.

Additional bands (not shown) may be arranged on second support layer 100a, for example, in the same manner as bands 201–206 are arranged on support layer 100. Pull string 801 may include additional knots to deploy the additional bands (represented by knot 501a). These additional bands may, for example, be placed on the ligating band dispenser prior to bands 201–206. Bands 201–206 may then be arranged as described above. In this manner, band 206 will, for example, be deployed first, followed by bands 201–205 in descending order. After bands 201–206 are deployed, the additional knots will deploy the additional bands, for example one at a time as described above, until all bands are deployed.

Figure 4:
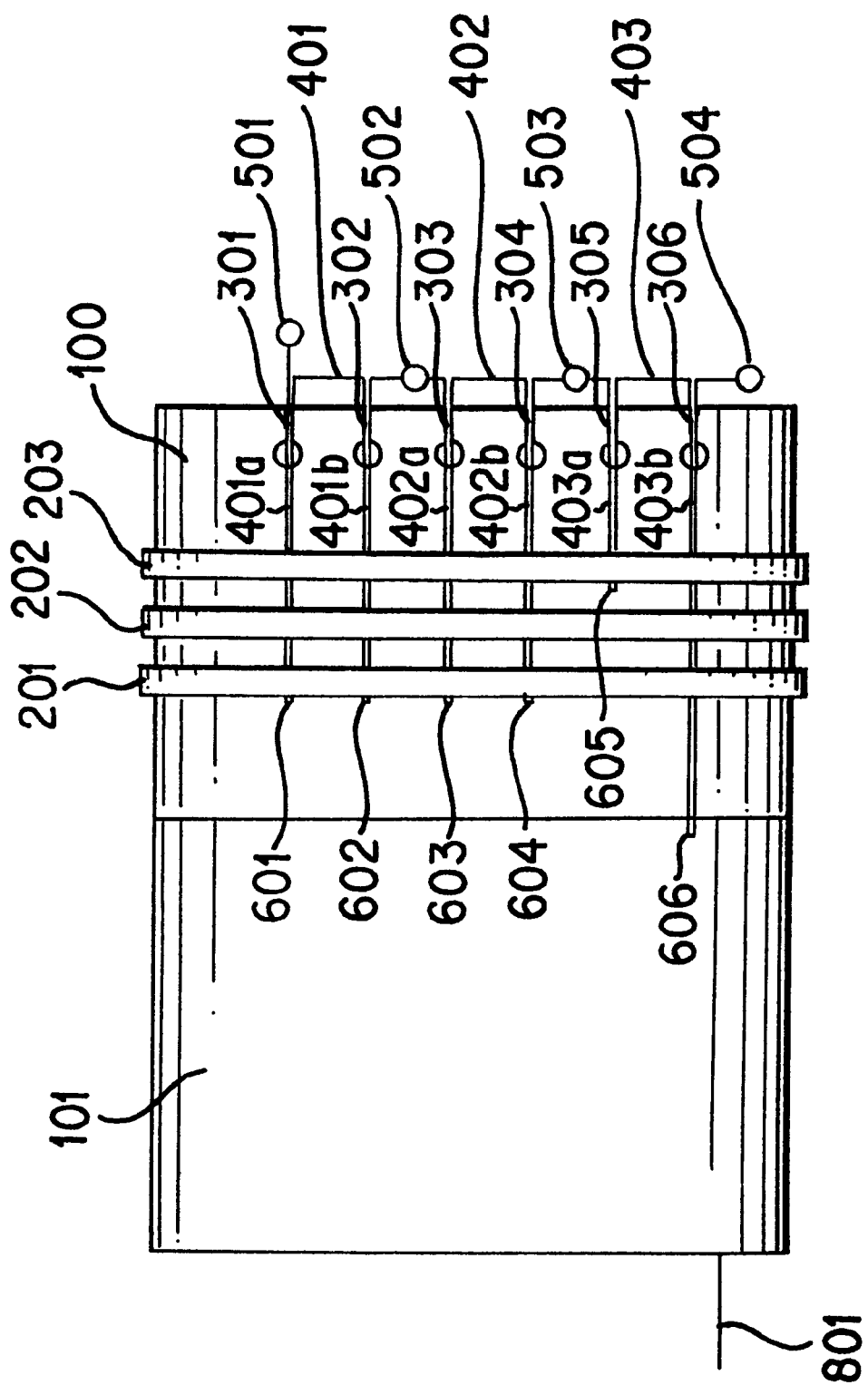
FIG. 4 is a side view of another exemplary ligating band dispenser according to the present invention having an alternate arrangement of the pull string and the ligating bands.
Figure 5:
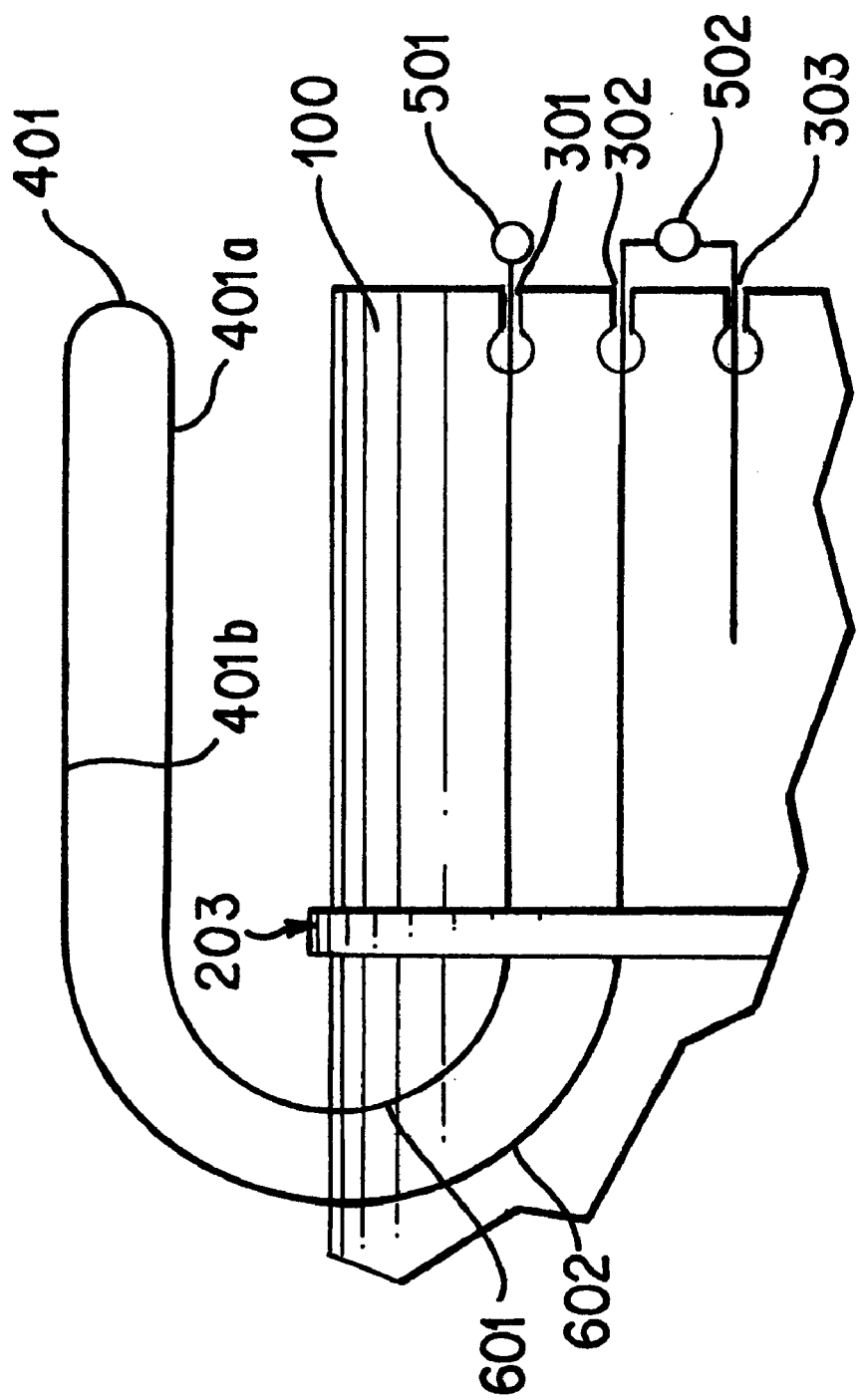
FIG. 5 is a side view of an exemplary ligating band dispenser according to the present invention utilizing a second exemplary pull string arrangement.

FIGS. 4 and 5 illustrate an alternative arrangement of the bands and pull string 801. The dispenser of FIG. 4 deploys, for example, three bands 201–203. Accordingly, pull string 801 includes, for example, only four knots 501–504, separated by three string segments 401–403. The dispenser, however, still includes, for example, six slots 301–306. To arrange bands 201–203, knot 501 and knot 502 are placed and retained, for example, behind slots 301 and 303, respectively. String segment 401, which forms a loop with knots 501 and 502 retained, is extended proximally and placed against the external face of the support surface 100. Band 201 may then be stretched over support surface 100 and placed over string segment 401. With band 201 in place, string segment 401 may be folded, for example, back over band 201 and looped between slots 501 and 502, as shown in FIG. 5. This arrangement forms two loops 401a and 401b around band 201, which will both urge band 201 distally when the pull string 801 is drawn towards the operator.

Two slack portions 601 and 602 of loops 401a and 401b are also formed. These may lay proximally against the external face of the support surface 100, and may, for example, be of equal length. Alternatively, slack portion 602 may be pulled proximally, thereby extending slack portion 602 and decreasing slack portion 601 until slack portion 601 is minimized (i.e. until loop 401a has no slack portion 601). In this manner, when band 201 is deployed, all the slack portions 601 and 602 will be taken up before either loop 401a or loop 401b applies a force to band 201.

Once band 201 is placed on the support surface 100, the pull string 801 may be threaded up slot 303 and back down slot 304, and knot 503 may be retained, for example, behind slot 305. String segment 402 is extended, for example, proximally along the external face of the support surface 100, and band 202 is then placed over string segment 402. With band 202 in place, string segment 402 may be folded back over band 202 and looped around slots 503 and 504. This creates loops 402a and 402b and slack portions 603 and 604, which may be arranged as described above. Slack portion 603, slack portion 604, or both may be tucked, for example, under band 201.

Band 203 may be similarly placed on the support surface 100. Knot 504 may be retained behind slot 306 to prevent, for example, distal migration of the pull string 801. In addition, slack portion 605, slack portion 606, or both may each be tucked, for example, under band 201, 202, or both.

Note that outer casing 103, while not shown in FIGS. 4 and 5, may be included in this exemplary embodiment. Other elements not specifically described in conjunction with this particular exemplary embodiment may also be included. It can be understood that this is generally true for each exemplary embodiment described herein: for purposes of clarity, certain elements shown in one pictured embodiment may not appear in other pictured embodiments, but these elements may be included when not shown if desired.

Figure 6:
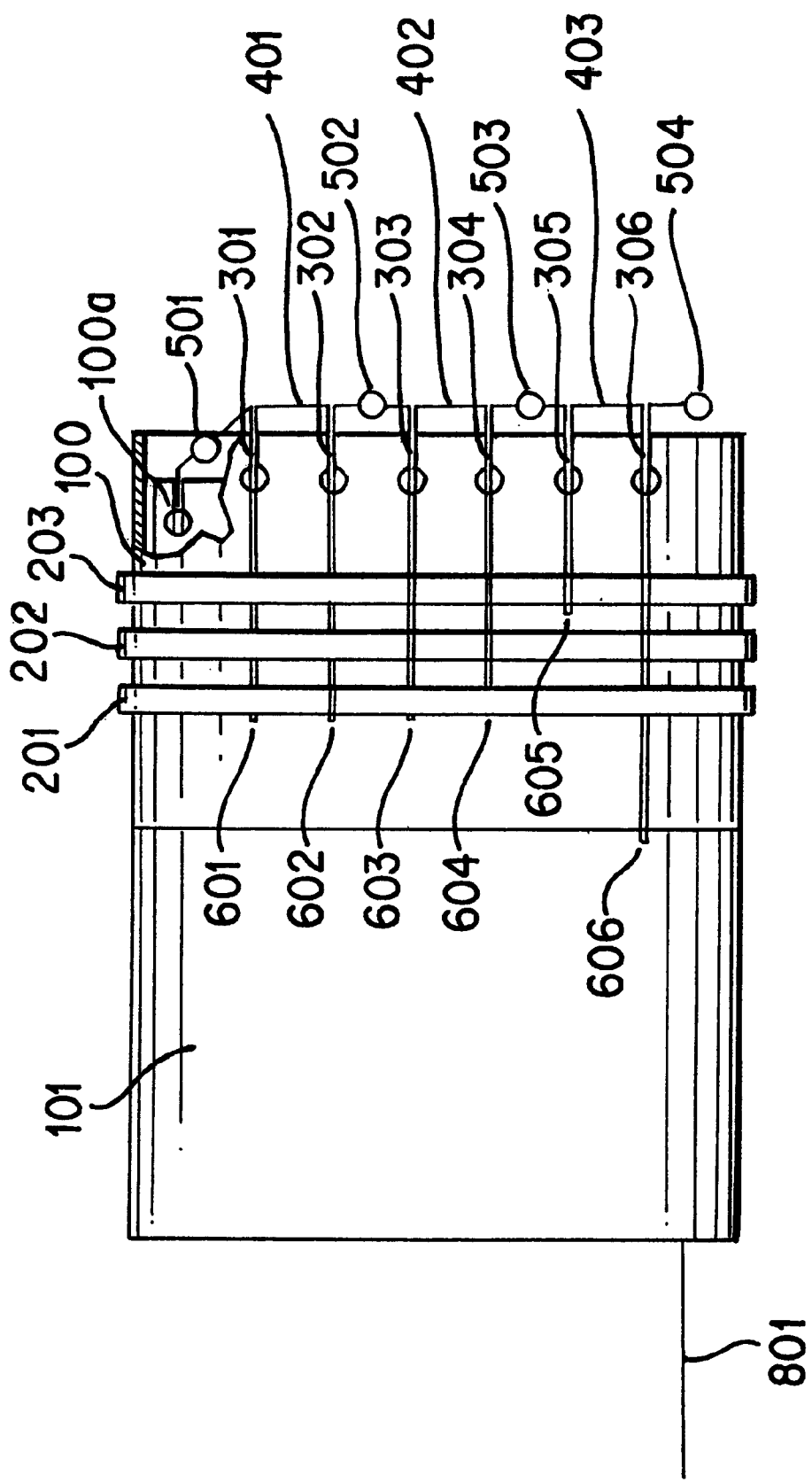
FIG. 6 is a partially cut away side view of another exemplary ligating band dispenser utilizing the pull string arrangement of FIG. 5.

FIG. 6 illustrates an exemplary ligating band dispenser with the band/pull line arrangement of FIGS. 4 and 5, having, for example, a second support layer 100a. The second support layer 100a shown in FIG. 6 may have, for example, the same structure as the second support layer of FIG. 3. Likewise, the arrangement of the second support layer 100a of FIG. 6 is analogous to the arrangement of the second support layer of FIG. 3. Specifically, additional bands (not shown) may be placed on second support layer 100a using, for example, the arrangement described above with respect to the embodiment of FIGS. 4 and 5. Once the additional bands have been loaded, bands 201–203 may be loaded, for example, as described with respect to the embodiment of FIGS. 4 and 5. In use, band 203 will, for example, be deployed first, followed by bands 202 and 201. The additional bands may then be deployed, with the distal-most additional band being deployed first, for example, followed by the remaining additional bands.

Figure 7:
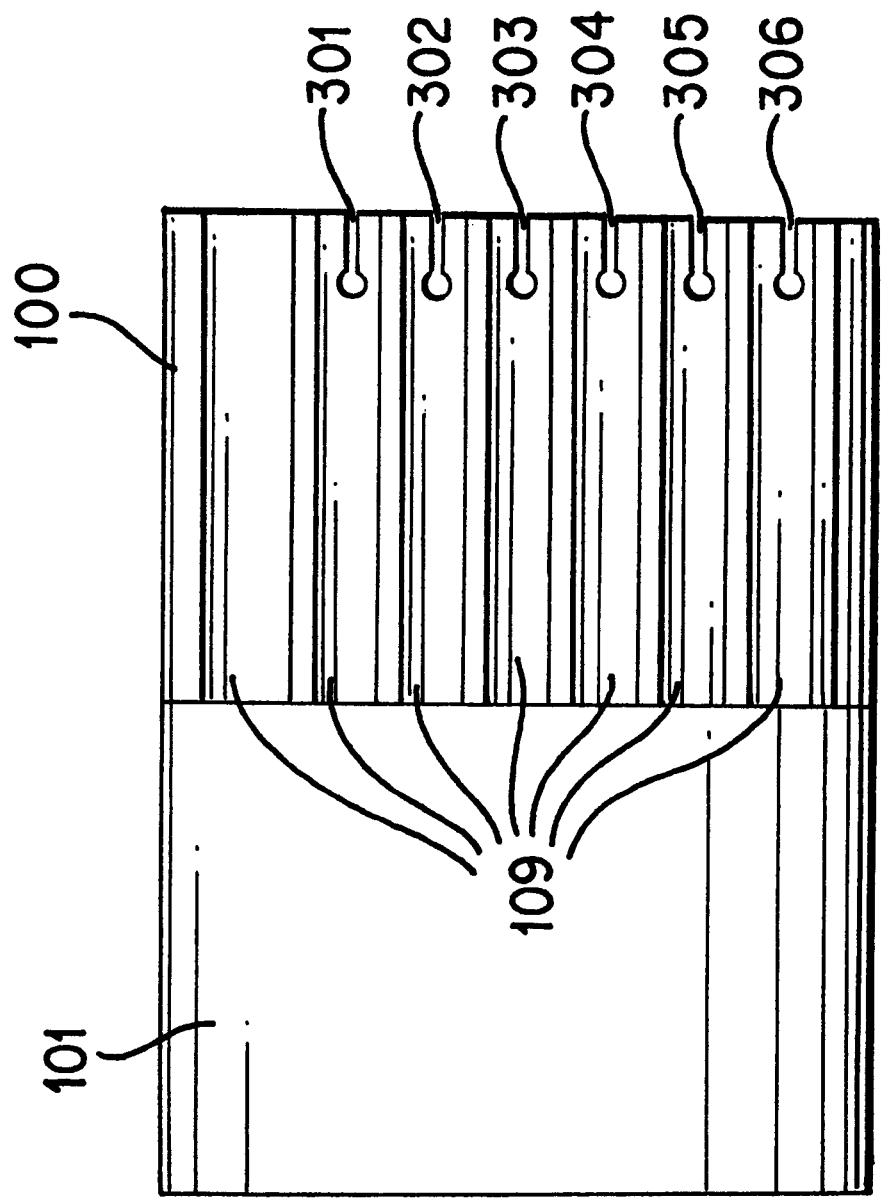
FIG. 7 is a side view of an exemplary ligating band dispenser according to the present invention having a plurality of grooves on an external face.
Figure 8:
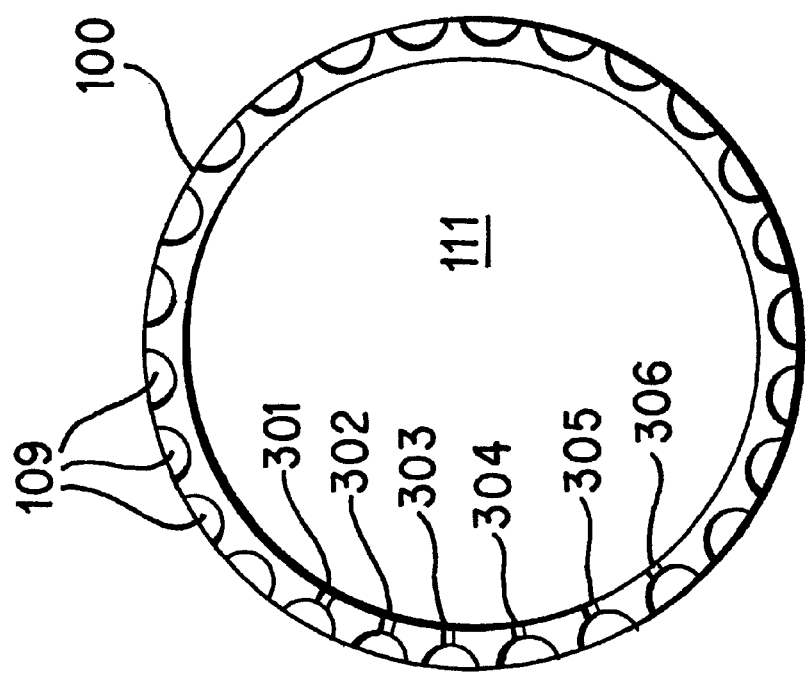
FIG. 8 is an end view of the ligating band dispenser of FIG. 7.

FIGS. 7 and 8 illustrate another exemplary embodiment of a ligating band dispenser according to the present invention, the ligating band dispenser including a plurality of axially-running grooves 109 formed on the external face of support surface 100. Grooves 109, which reduce friction between bands 201–206 (not shown) and support surface 100, are formed, for example, around the entire circumference of support surface 100. In addition, slots 301–306 may each be aligned, for example, along the center of one of grooves 109.

Figure 9:
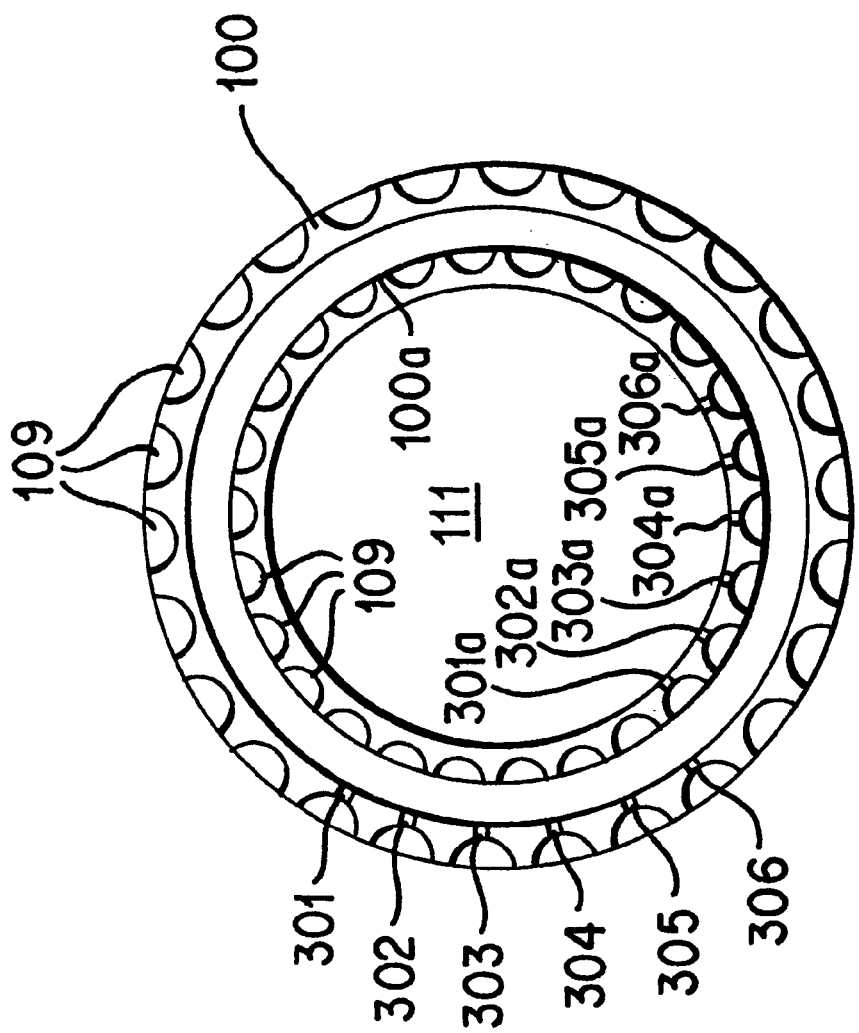
FIG. 9 in an end view of an exemplary embodiment of a two-layer ligating band dispenser according to the present invention having a plurality of grooves on the external faces.

FIG. 9 shows an end view of a ligating band dispenser having grooves 109 of FIGS. 7 and 8. The exemplary embodiment of FIG. 9 includes a second support surface 100a. As with the embodiment of FIGS. 7 and 8, slots 301–306, as well as slots 301a–306a of support surface 100a, may be aligned, for example, with grooves 109. Moreover, slots 301–306 may, as a group, be circumferentially offset from slots 301a–306a. This offset allows the pull wire 801, for example, to traverse the slots 301–306, 301a–306a without excessive circumferential motion. In addition, the relatively small distance between slots 306 and 301a eliminates the possibility of the pull string 801 not having sufficient length to loop around the bands associated with slots 306 and 301a.

FIGS. 10–13 illustrate further exemplary embodiments of a ligating band dispenser according to the present invention. The embodiments shown in FIGS. 10–13 may deploy, for example, six bands 201–206, but a greater of lesser number of bands may be included. In these embodiments, support surface 100 does not, for example, include any of slots 301–306 to retain knots 501–506. Instead, knots 501–506 are actively employed, for example, to urge bands 201–206 towards the distal end of support surface 100 for deployment.

Figure 10:
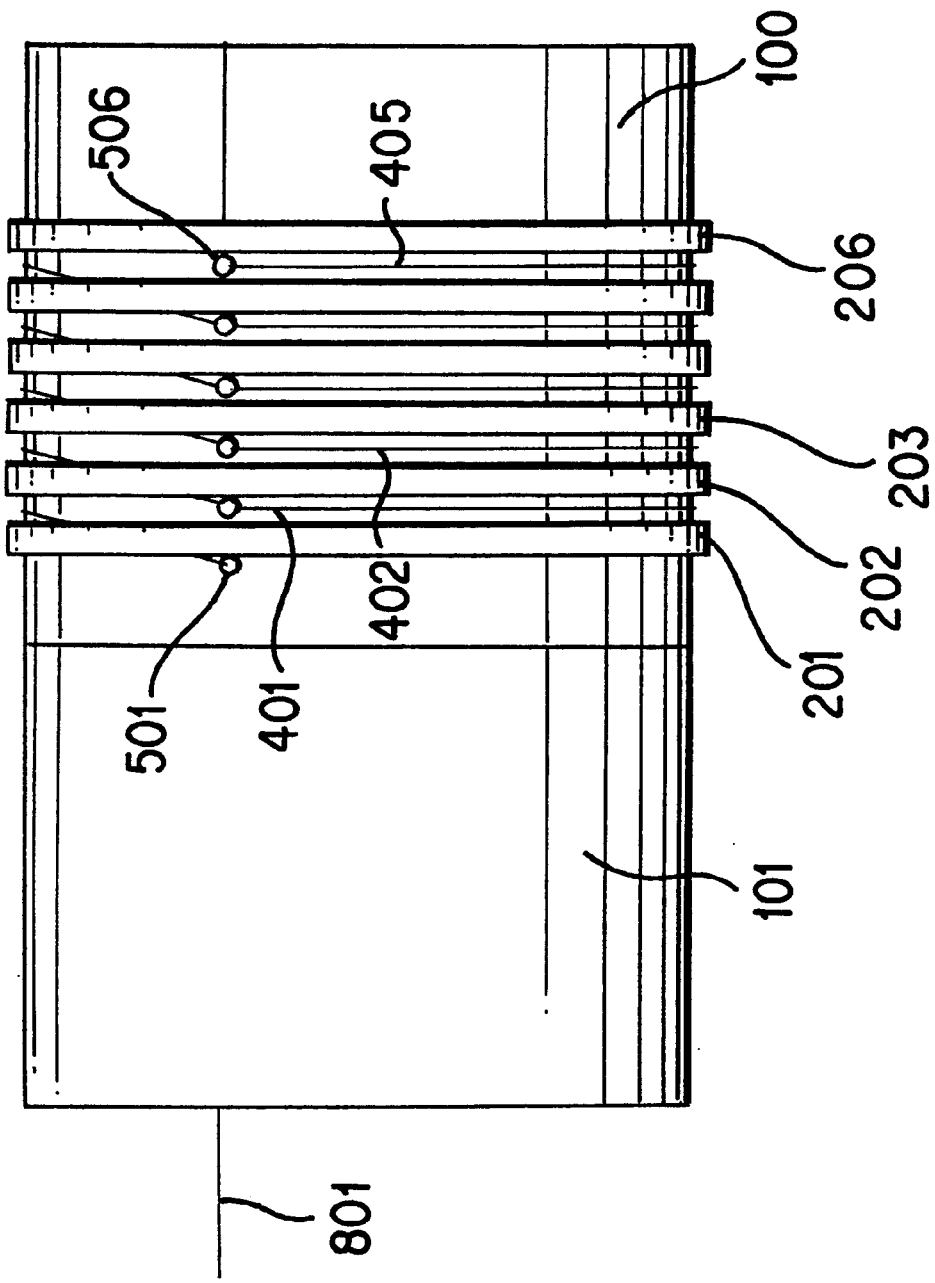
FIG. 10 is a side view of an exemplary ligating band dispenser according to the present invention utilizing a third exemplary pull string arrangement.

In the embodiment of FIG. 10, in order to arrange bands 201–206 and pull string 801, knot 501 of pull string 801 is arranged, for example, on the external face of support surface 100, with pull string 801 extending from knot 501 distally along support surface 100. As shown in FIG. 10, knot 501 is disposed, for example, at the extreme distal end of pull string 801. Band 201 may then be stretched over support surface 100 and pull string 801, and placed over pull string 801 just distal of knot 501. Pull string 801 is then wound, for example, around support surface 100, for example clockwise when viewed from the distal end of the ligating band dispenser, so that knot 501 rests distal of band 201. The length of string segments 401–405 may be such that the pull string 801 winds, for example, approximately once around support surface 100 before the next knot (in this case, knot 502) rests against support surface 100.

Once knot 502 rests against support surface 100, band 202 may be stretched over support surface 100 and placed over pull string 801 just distal of knot 502. Again, pull string 801 may be wound, for example, around support surface 100 until knot 503 rests against support surface 100, at which point band 203 may be placed over pull string 801 just distal of knot 503. This process may continue until all bands 201–206 are arranged on the support surface 100.

To deploy bands 201–206, the ligating band dispenser may be placed over a lesion as described above and the lesion may be drawn into the distal end of the ligating band dispenser as known in the art. Once in place, pull string 801 may be drawn, for example, proximally through the endoscope (not shown) towards an operator. As pull string 801 is drawn proximally, knot 506 will be drawn distally along support surface 100, contacting band 206 and pulling band 206 towards the distal end of support surface 100 and eventually deploying band 206. As knot 506 is pulled, pull string 801 unwinds, for example, around support surface 100, taking up any slack in pull string 801. After band 206 is deployed and any slack taken up (which may be accomplished, for example, with one turn of a spool taking up pull string 801), the ligating band dispenser is ready to deploy band 205.

As described above, when the ligating band dispenser is fixed to the distal end of an endoscope, the support surface 100 is preferably oriented so that the point where the string 801 extends from the distal rim of the support surface 100 is as close as possible to the lumen of the endoscope through which the string 801 extends back to the operator. This ensures that the string 801 does not interfere with either the field of vision or the drawing of tissue into the channel 111. This also allows the operator to employ the lumen to introduce other devices to the distal end of the endoscope.

Figure 11:
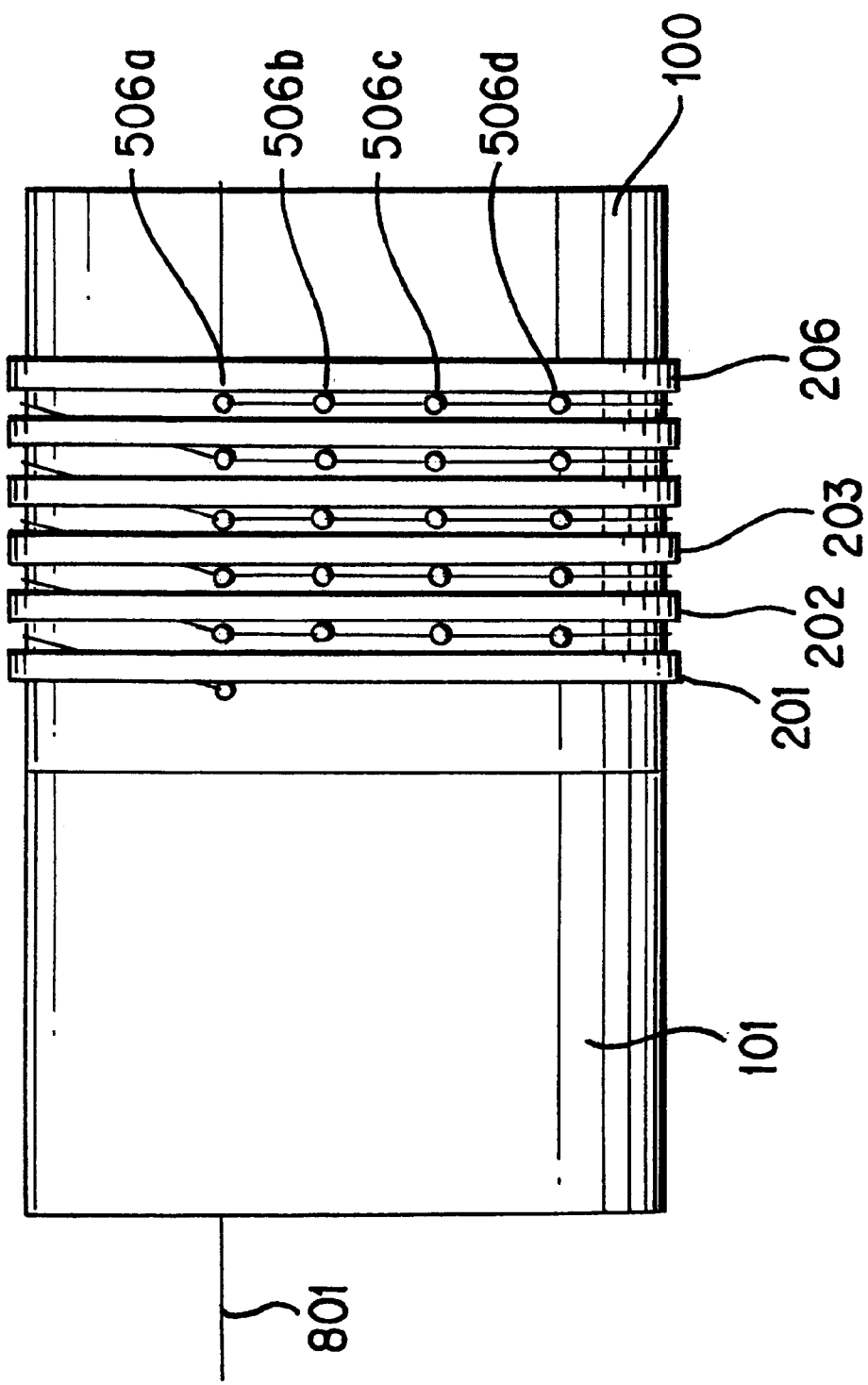
FIG. 11 is a side view of an exemplary ligating band dispenser according to the present invention utilizing a fourth exemplary pull string arrangement.

FIG. 11 illustrates another exemplary embodiment of a ligating band dispenser having an arrangement similar to the dispenser of FIG. 10. In the embodiment shown in FIG. 11, however, a plurality of knots may be employed between each pair of bands 201–206. For example, knot 506 of FIG. 10 corresponds to knots 506a–506d of FIG. 11. These additional knots ensure that even if one of knots 506a–506d (e.g. knot 506a in FIG. 11) slips under band 206, band 206 will not be stranded on support surface 100. Of course, more or less than four knots may be used. In addition, although FIG. 11 shows only one knot behind band 201, additional knots may be included behind band 201 as well.

Figure 12:
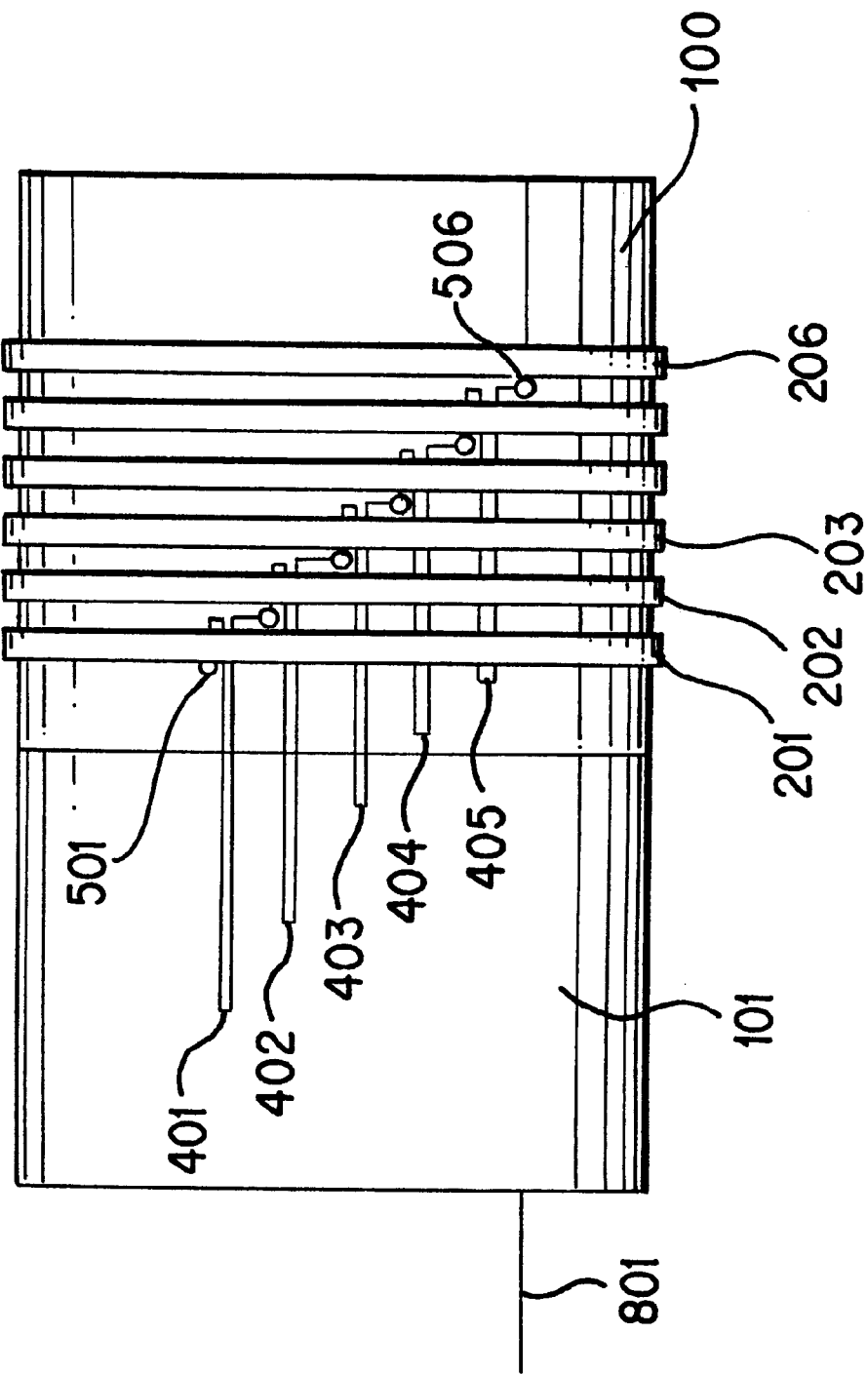
FIG. 12 is a side view of an exemplary ligating band dispenser according to the present invention utilizing a fifth exemplary pull string arrangement.
Figure 13:
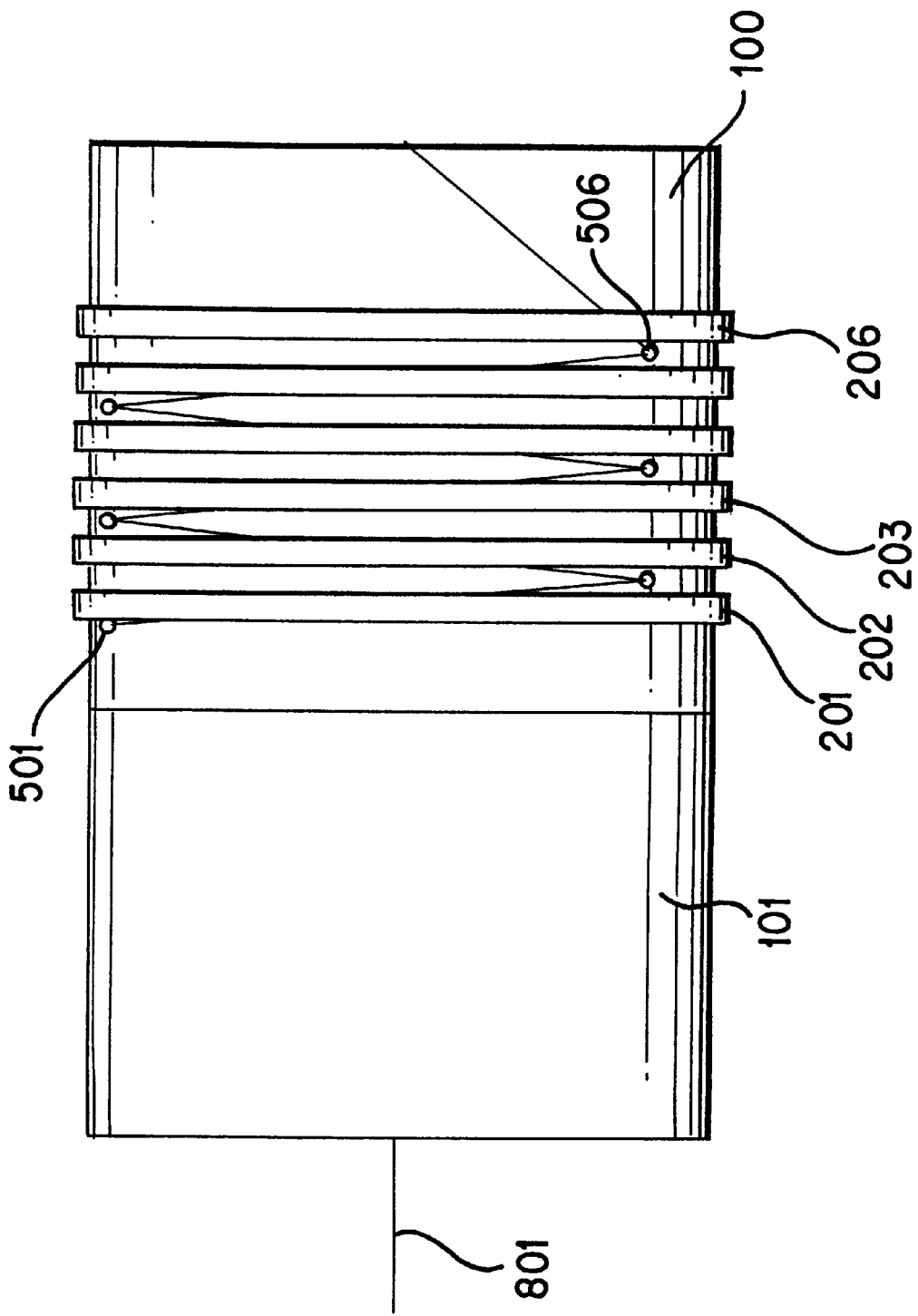
FIG. 13 is a side view of an exemplary ligating band dispenser according to the present invention utilizing a sixth exemplary pull string arrangement.

FIGS. 12 and 13 illustrate alternative arrangements of string segments 401–405, which essentially form slack between knots 50–506. In the arrangement of FIG. 12, string segments 401–405 are, for example, looped and arranged proximally along support surface 100. These may be tucked, for example, under any bands proximal to the corresponding knot, tucked under all such bands, or lain over top of such bands. In the arrangement of FIG. 13, string segments 401–405 are wound, for example, around support surface 100 as in FIG. 10. In the arrangement of FIG. 13, however, the direction of winding changes for each consecutive string segment 401–405, creating a "zig-zag" path of the pull string 801.

Figure 14:
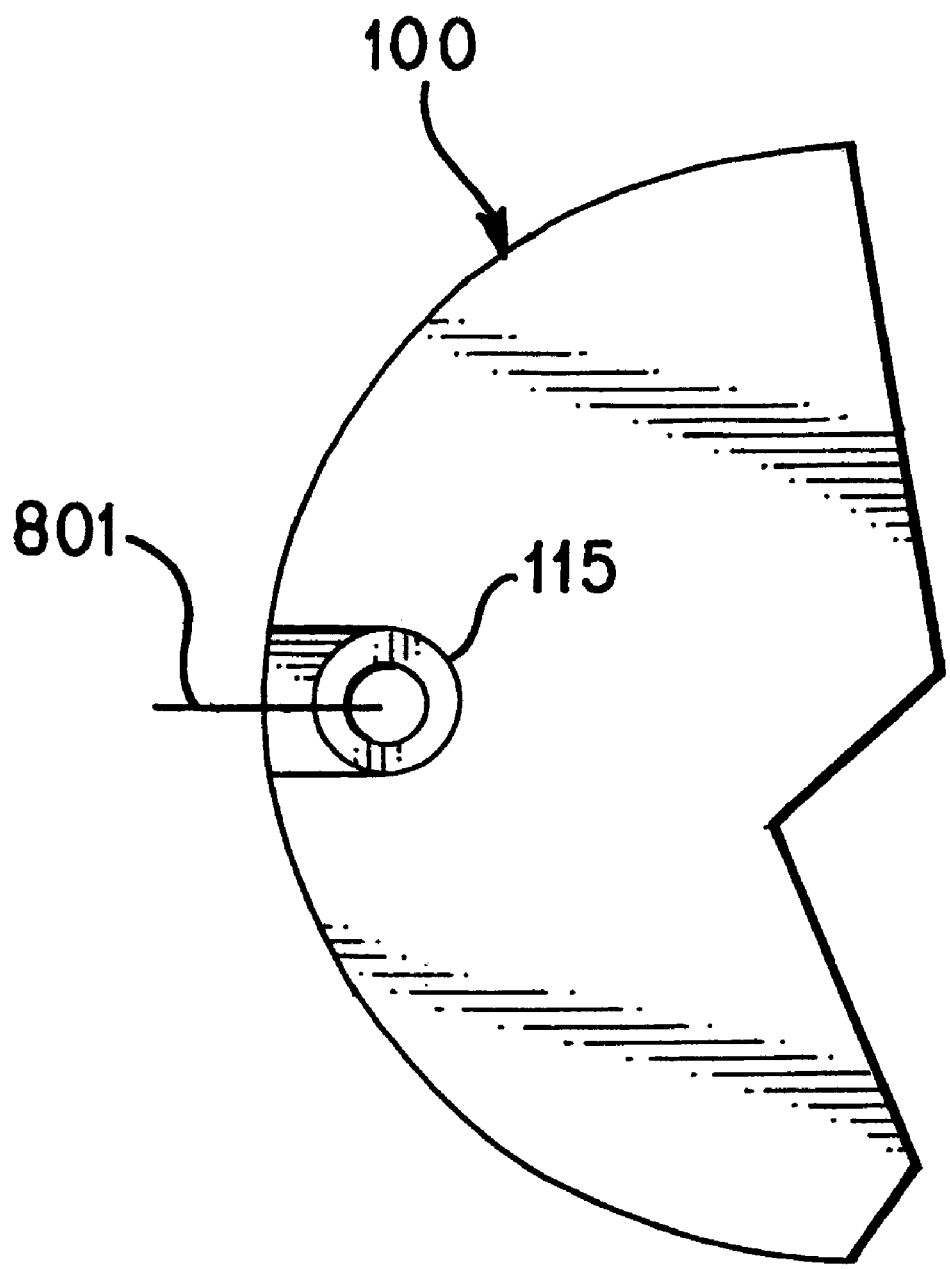
FIG. 14 is a cross-sectional view of an exemplary ligating band dispenser including a guide ring for a pull string.

FIG. 14 illustrates a further exemplary feature of a ligating band dispenser according to the present invention, a guide ring 115. To prevent any precession of the pull string 801 around the support surface 100, pull string 801 may be threaded, for example, through guide ring 115. Guide ring 115 may be disposed, for example, on the internal face of support surface 100 (i.e. within channel 111). Guide ring 115 may, of course, be present in any of the embodiments described above.

The present invention has been described with respect to several exemplary embodiments. There are many modifications of the disclosed embodiments which will be apparent to those of skill in the art. It is understood that these modifications are within the teaching of the present invention which is to be limited only by the claims.

What is claimed is:

1. A ligating band dispenser, comprising:
   a substantially cylindrical first support surface capable of holding a plurality of first ligating bands, the first support surface having a first channel extending substantially axially therethrough, wherein a plurality of first slots extend away from a distal end of the first support surface through at least a portion of the first support surface; and a pull line having a plurality of first abutting portions, each of the first abutting portions having a diameter greater than a diameter of the pull line, the first abutting portions defining a plurality of first segments therebetween, wherein the pull line extends through the first slots with each of the first abutting portions being retained within the first channel by contact with a corresponding one of the first slots and wherein each of the first segments loops around a corresponding one of the first ligating bands.

2. The ligating band dispenser according to claim 1, further comprising an adaptor disposed at a proximal end of the first support surface for coupling the first support surface to an endoscope.

3. The ligating band dispenser according to claim 1, further comprising a substantially cylindrical casing surrounding the first support surface and the first ligating bands, a proximal portion of the casing being connected to a proximal portion of the first support surface.

4. The ligating band dispenser according to claim 3, wherein the casing includes an outlet hole formed in a distal portion of the casing and an inlet hole formed in the proximal portion of the casing, the pull line exiting the casing through the outlet hole and entering the casing through the inlet hole.

5. The ligating band dispenser according to claim 1, wherein a plurality of axially running first grooves are formed in an external face of the first support surface.

6. The ligating band dispenser according to claim 5, wherein each of the first slots is disposed along a centerline of a corresponding one of the first grooves.

7. The ligating band dispenser according to claim 1, wherein the first support surface further includes a guide ring disposed on an interior face thereof, the pull line being threaded through the guide ring.

8. The ligating band dispenser according to claim 1, further comprising a substantially cylindrical second support surface substantially coaxial with the first support surface, the second support surface having a second channel extending substantially axially therethrough and holding a plurality of second ligating bands thereon, wherein a plurality of second slots extend away from a distal end of the second support surface through at least a portion thereof, and wherein the pull line includes a plurality of second abutting portions defining a plurality of second segments therebetween, wherein the pull line extends through the second slots with each of the second abutting portions being retained within the second channel by contact with a corresponding one of the second slots and wherein each of the second segments loops around a corresponding one of the second ligating bands.

9. The ligating band dispenser according to claim 8, wherein the second support surface is disposed within the first support surface.

10. The ligating band dispenser according to claim 9, wherein the first and second support surfaces are coupled to one another, further comprising an adaptor coupled to a proximal portion of at least one of the first and second support surfaces for coupling the first and second support surfaces to an endoscope.

11. The ligating band dispenser according to claim 9, further comprising a substantially cylindrical casing surrounding the first support surface and the first ligating bands, a proximal portion of the casing being connected to a proximal portion of the first support surface.

12. The ligating band dispenser according to claim 11, wherein the casing includes an outlet hole formed in a distal portion of the casing and an inlet hole formed in the proximal portion of the casing, the pull line exiting the casing through the outlet hole and entering the casing through the inlet hole.

13. The ligating band dispenser according to claim 9, wherein a plurality of axially running first grooves extend across at least a portion of an external face of the first support surface, and a plurality of axially running second grooves extend across at least a portion of an external face of the second support surface.

14. The ligating band dispenser according to claim 13, wherein each of the first slots is disposed along a centerline of a corresponding one of the first grooves, and each of the second slots is disposed along a centerline of a corresponding one of the second grooves.

15. The ligating band dispenser according to claim 9, wherein the second support surface further includes a second guide ring disposed on an interior face thereof, the pull line being threaded through the second guide ring.

16. A ligating band dispenser, comprising:
    a substantially cylindrical first support surface capable of holding a plurality of first ligating bands thereon, the first support surface having a substantially cylindrical first channel extending substantially axially therethrough, and the first support surface having a plurality of first slots extending away from a distal end through at least a portion of the first support surface; and
    a pull line having a plurality of first knots, the plurality of first knots defining a plurality of first segments therebetween, the pull line being arranged so that each of the plurality of first knots is retained behind a corresponding one of the plurality of first slots;
    wherein each of the first segments is looped around a corresponding one of the first ligating bands, looped through a pair of first slots, and looped again around the corresponding one of the first ligating bands.

17. The ligating band dispenser according to claim 16, further comprising an adaptor coupled to a proximal end of the support surface for coupling the first support surface to an endoscope.

18. The ligating band dispenser according to claim 16, further comprising a substantially cylindrical casing surrounding the first support surface and the first ligating bands, a proximal portion of the casing being connected to a proximal portion of the first support surface.

19. The ligating band dispenser according to claim 18, wherein the casing includes an outlet hole formed in a distal portion of the casing and an inlet hole formed in the proximal portion of the casing, the pull line exiting the casing through the outlet hole and entering the casing through the inlet hole.

20. The ligating band dispenser according to claim 16, wherein a plurality of axially running grooves are formed in an external face of the first support surface.

21. The ligating band dispenser according to claim 20, wherein each of the first slots is disposed along a centerline of a corresponding one of the first grooves.

22. The ligating band dispenser according to claim 16, wherein the first support surface further includes a guide ring disposed on an interior face thereof, the pull line being threaded through the guide ring.

23. The ligating band dispenser according to claim 16, further comprising a substantially cylindrical second support surface substantially coaxial with the first support surface, wherein the second support surface holds a plurality of second ligating bands thereon and includes a plurality of second slots extending away from a distal end of the second support surface a predetermined distance, wherein the pull line includes a plurality of second knots defining a plurality of second segments therebetween, wherein the pull line extends through the second slots with each of the second knots being retained within the second channel by contact with a corresponding one of the second slots and wherein each of the second segments loops around a corresponding one of the second ligating bands.

24. The ligating band dispenser according to claim 16, wherein the first segments are consecutively wound around the first support surface in opposite rotational directions.

25. The ligating band dispenser according to claim 16, wherein each of the first segments is looped and arranged proximally along an external face of the first support surface.

26. The ligating band dispenser according to claim 25, wherein at least one of the first segments is tucked under a proximal-most one of the first ligating bands.

27. The ligating band dispenser according to claim 16, wherein at least two of the first knots are retained proximally of each one of the first ligating bands.

28. A ligating band dispenser, comprising:
   a substantially cylindrical support surface having a substantially cylindrical channel extending substantially axially therethrough, the support surface having an outer surface and a distal end;
   a plurality of ligating bands supported on the outer face of the support surface; and
   a single pull line having a plurality of knots formed thereon, the pull line extending through the cylindrical channel, around the distal end at most once, and generally proximally and circumferentially along the outer surface of the support surface, wherein each of the knots is retained proximally of a corresponding one of the ligating bands so that when the pull line is operated to draw a ligating band from the support surface at least one knot pushes a distal most one of the ligating bands off the distal end of the support surface;
   wherein the pull line extends from a first one of the knots around the support surface by a predetermined distance before passing underneath a next most distal band where a second one of the knots is seated against a proximal surface of the next most distal band, the predetermined distance being selected to provide a desired amount of slack between the first and second knots so that, upon distal motion of the first knot, the second knot does not move until after the distal most ligating band has been pushed off the distal end of the support surface.

29. The ligating band dispenser according to claim 28, wherein a plurality of secondary knots are disposed along the pull line between the first and second knots.

30. A method of ligating lesions within a living body comprising the steps of:
   inserting into the body a device including:
      a substantially cylindrical support surface having a plurality of ligating bands received thereon, the support surface being coupled to a distal end of an endoscope, wherein an aspiration chamber extends substantially axially through the support surface to communicate with a working channel of the endoscope, wherein a plurality of slots extend away from a distal end of the support surface through at least a portion of the support surface; and
      a single pull line extending through the working channel of the endoscope, through the aspiration chamber to releasably couple to each of the ligating bands, wherein the pull line defines a plurality of abutting portions, each of the abutting portions having a diameter greater than a diameter of the pull line, wherein the pull line extends through the slots with each of the abutting portions being retained within the channel by contact with a corresponding one of the slots;
   positioning a distal end of the support surface adjacent to a first lesion to be ligated;
   advancing a tool through the working channel of the endoscope;
   drawing the first lesion into the aspiration chamber by one of application of suction and the use of a gripping device; and
   drawing the pull line proximally from the working channel of the endoscope to release a selected first one of the ligating bands from the support surface to ligate the first lesion.

31. The method according to claim 30, wherein the tool advanced through the working channel is a sclerotherapy needle.

32. The method according to claim 30, further comprising the steps of:
   after the first lesion has been ligated, positioning the distal end of the support surface adjacent to a second lesion to be ligated; and
   drawing the pull line proximally from the working channel of the endoscope to release a selected second one of the ligating bands from the support surface to ligate the second lesion.

* * * * *